United States Patent [19]
Wheeler et al.

[11] Patent Number: 5,541,091
[45] Date of Patent: Jul. 30, 1996

[54] PROCESS FOR THE BIOCATALYTIC COUPLING OF AROMATIC COMPOUNDS IN THE PRESENCE OF A RADICAL TRANSFER AGENT

[75] Inventors: Thurman M. Wheeler, Columbus; Joseph Borovsky, Bexley; Alexander Pokora, Pickerington, all of Ohio

[73] Assignee: Enzymol International, Inc., Columbus, Ohio

[21] Appl. No.: 417,230

[22] Filed: Apr. 5, 1995

[51] Int. Cl.[6] ............................................. C12P 7/22
[52] U.S. Cl. ...................... 435/128; 435/129; 435/130; 435/136; 435/147; 435/155; 435/156; 435/192; 527/200; 528/86; 528/210; 528/212
[58] Field of Search .................................. 435/155, 156, 435/147, 192, 128, 129, 130, 136; 528/86, 210, 212; 527/200

[56] References Cited

U.S. PATENT DOCUMENTS

| | | | |
|---|---|---|---|
| 4,647,952 | 3/1987 | Pokora et al. | 346/210 |
| 4,900,671 | 2/1990 | Pokora et al. | 435/156 |
| 5,147,793 | 9/1992 | Johnson et al. | 435/156 |
| 5,188,953 | 2/1993 | Johnson et al. | 435/156 |

OTHER PUBLICATIONS

Klibanov et al. "Enzymatic Removal of Toxic Phenols and Analines from Waste Water" J. Applied Biochem. 2, pp. 414–421 (1980).

*Primary Examiner*—Herbert J. Lilling
*Attorney, Agent, or Firm*—Thompson Hine & Flory P.L.L.

[57] ABSTRACT

A process is described for the dimerization of a substituted aromatic compound of the formula (I):

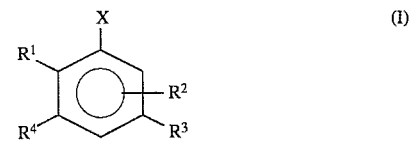

wherein X represents —OH, —SH or —NHR where R is H, an alkyl group or an aryl group; $R^1$ and $R^2$ represent an alkyl group, an aryl group, an alkenyl group, an alkynyl group, an alicyclic group, a halogen atom, an alkoxy group, an aryloxy group, a hydroxy group, or an amino group; and $R^3$ and $R^4$ can have the same definition as $R^1$ and $R^2$ and may additionally represent a hydrogen atom; which comprises reacting the substituted aromatic compound in the presence of a peroxidase enzyme, a peroxide and a radical transfer agent in an aqueous medium.

14 Claims, No Drawings

PROCESS FOR THE BIOCATALYTIC COUPLING OF AROMATIC COMPOUNDS IN THE PRESENCE OF A RADICAL TRANSFER AGENT

BACKGROUND OF THE INVENTION

The present invention relates to a process for the biocatalytic coupling of aromatic compounds such as phenols, thiophenols and anilines and, particularly, to a process for coupling sterically hindered aromatic compounds in the presence of a peroxidase enzyme, a peroxide and a radical transfer agent to provide the corresponding dimer.

The biocatalytic oxidative coupling of phenols using horseradish or soybean peroxidase is disclosed in U.S. Pat. No. 4,900,671 to Pokora et al. and U.S. Pat. No. 5,188,953 to Johnson et al. The dimerization of dialkyl and diarylphenols such as 2,4-dialkylphenol and 2,6-dialkylphenol is discussed in copending U.S. application Ser. No. 08/379,202 filed Jan. 27, 1995.

Klibanov et al. "Enzymatic Removal of Toxic Phenols and Anilines from Waste Waters" J. of Appl. Biochem. 2, 414–421 (1980) teaches the horseradish peroxidase-assisted polymerization and precipitation of phenols and anilines from waste water and further discloses that the removal of some phenols which are difficult to remove from waste water can be enhanced by the presence of other easily removable phenols. The products are considered to be mixed polymers containing both hard to remove phenols and easily removable phenols.

SUMMARY OF THE INVENTION

The present invention is an improvement in the processes taught in U.S. Pat. Nos. 4,900,671 and 5,188,953 wherein certain aromatic compounds that do not react with peroxidases or react poorly with peroxidases possibly because they can not reach the active site of the enzymes efficiently (for example, due to steric hinderance) can be reacted through the introduction of a radical transfer agent. In accordance with a particular embodiment of the present invention, 2,4 and 2,6-disubstituted aromatic compounds are reacted in the presence of a peroxidase, peroxide and a radical transfer agent to provide dimers in excellent yield.

The invention is particularly useful in the reaction of 2,4- and 2,6-disubstituted aromatic compounds that do not react by themselves with peroxidases, presumably due to sterically hindered groups near the phenolic hydroxy. These compounds exhibit little or no reaction in the absence of the radical transfer agent. The radical transfer agent is characterized in that it is a substrate for the enzyme; it is not sterically hindered and can reach the active site of the enzyme where it is oxidized to form a radical. This radical reacts with the aromatic compound to abstract a hydrogen atom to produce a radical of the aromatic compound which dimerizes. Unexpectedly, the radical transfer agent does not appear to couple with the substituted aromatic compound in any significant amount. Little if any chemically bound radical transfer agent has been observed in the dimer product.

In a preferred embodiment of the invention, the aromatic compound is a 2,4- or 2,6-disubstituted phenol, thiophenol or aromatic amine such as aniline. The 2,4 or 2,6-aromatic compound is preferably reacted in the presence of soybean peroxidase and hydrogen peroxide using phenol as the radical transfer agent to provide the corresponding dimer.

The invention is particularly useful in converting 2,4 and 2,6-disubstituted phenols to 3,3',5,5'-tetrasubstituted-biphenyl- 2,2'-diol and 3,3',5,5'-tetrasubstituted biphenyl-4,4'-diol, respectively.

It is, therefore, an object of the present invention to provide a process for the dimerization of certain substituted aromatic monomers selected from the group consisting of phenols, thiophenols, and anilines, and particularly, for the dimerization of 2,4- or 2,6-disubstituted aromatic monomers to the corresponding tetrasubstituted dimers using phenol or other peroxidise substrates as a radical transfer agent.

It is another object of the present invention to provide a process for the dimerization of sterically hindered aromatic compounds such as a di-tert-alkyl substituted phenols, thiophenols and anilines in the presence of a peroxidase enzyme, a peroxide and a radical transfer agent in an aqueous medium.

Other objects and advantages of the present invention will become apparent from the following description and the appended claims.

DEFINITION

A "purpurogallin unit" of peroxide means the amount of peroxide which produces a change of 12 absorbance units measured at 1 cm path length in one minute at 420 nm when added to a solution containing 110 mM potassium phosphate, 44 mM pyrogallol and 8 mM hydrogen peroxide and having a pH of 6 (Sigma Chemical Co., Peroxidase Bulletin).

DETAILED DESCRIPTION OF THE INVENTION

In carrying out the present invention, an aromatic compound of formula (I) is reacted in the presence of a peroxidase, a peroxide and a radical transfer agent to provide the corresponding dimer. The aromatic compound is a substituted phenol, thiophenol or aniline which can generally be represented by formula (I):

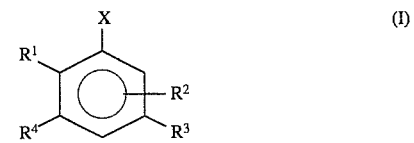

wherein X represents —OH, —SH or —NHR where R is H, an alkyl group or an aryl group; $R^1$ and $R^2$ represent an alkyl group, an aryl group, an alkenyl group, an alkynyl group, an alicyclic group, a halogen atom, an alkoxy group, an aryloxy group, a hydroxy group, a formyl group, or an amino group, such as a dialkylamino group or a diarylamino group; and $R^3$ and $R^4$ can have the same definition as $R^1$ and $R^2$ and may additionally represent a hydrogen atom. The invention is particularly useful in dimerizing 2,4 and 2,6-disubstituted aromatic compounds in which $R^3$ and $R^4$ are hydrogen. In a particularly useful aspect of the invention, the aromatic compound is a 2,4- or 2,6-disubstituted branched alkyl or aryl phenol and especially a 2,4- or a 2,6-di-t-butylphenol wherein the resulting diol is 3,3',5,5'-tetra-t-butyl-biphenyl-4,4'-diol. Those skilled in the art will also appreciate that while the substituted groups in a compound are typically the same, compounds having two different substituent groups and mixtures of different substituted aromatic compounds may be reacted as well.

While not wanting to be bound by any particular mechanism, it is proposed that the present invention involves the following schemes (A or B) which illustrate the dimerization reaction of a 2,4-disubstituted phenol (A) and a 2,6-disubstituted phenol (B):

A.

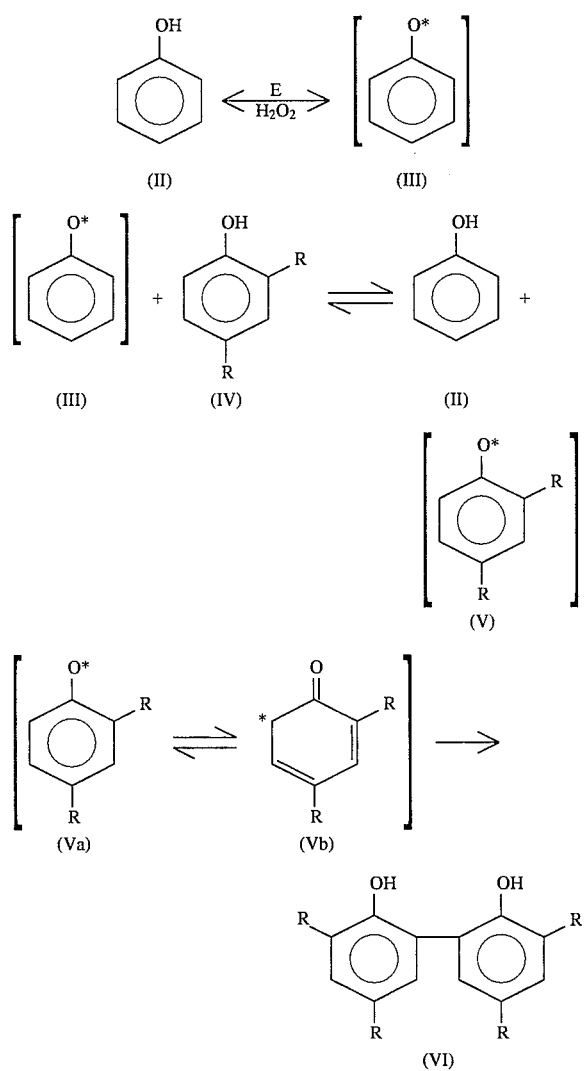

B.

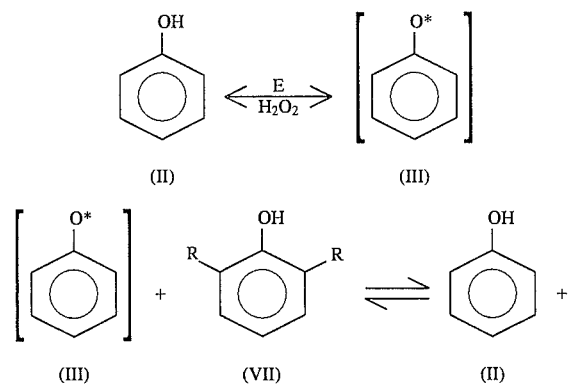

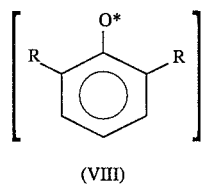

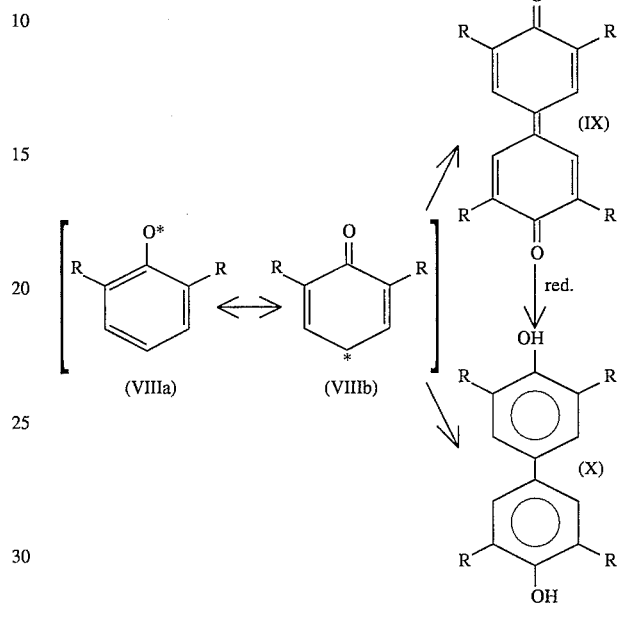

It is proposed that the enzyme E reacts with the phenol (II) to abstract the hydrogen from the hydroxy group creating a phenoxy radical (III). The phenoxy radical (III) then abstracts the phenolic hydrogen from the non-reactive or less reactive substituted phenolic substrate (IV) or (VII) to regenerate the phenol (II) and create a new substituted phenolic radical (V) or (VIII) (shown as resonant structures (Va) and (Vb) or (VIIIa) and (VIIIb)). In the reaction of the 2,4-disubstituted phenol, the reaction proceeds via structure (Vb) to produce the new dimer product (VI). In the reaction of the 2,6-disubstituted phenol, the reaction proceeds via structure (VIIIb) and may form the intermediate quinone (XI) which is then reduced by the monomeric substrate (VII) or the phenol (II) or the substituted phenolic radical (VIIIb) may go directly the corresponding dimer (X).

A number of different procedures may be used in carrying out the reaction of the aromatic substrate. Solutions of the aromatic substrate, enzyme, and peroxide may be individually prepared and metered into a reaction vessel, or solutions of the aromatic substrate and enzyme may be pre-mixed and the peroxide gradually added thereto. Alternatively, the enzyme and the aromatic substrate may be dissolved in a common solvent and the peroxide added later. Those skilled in the art will appreciate that a number of different reaction/mixing sequences are useful. In a preferred procedure, the peroxide is added at a controlled rate which is approximately equal to the rate at which it is consumed such that the concentration of the peroxide does not build to a level at which it undesirably inhibits the reaction and inactivates the enzyme. In general, the reaction is carried out by adding the substituted aromatic substrate and the radical transfer agent to the reaction medium which contains the peroxidase enzyme. The peroxide is added at a predetermined rate until the reaction is complete or nearly complete. Smaller quantities of radical transfer agent can be used by metering in the radical transfer agent at an appropriate concentration and rate which may be the same rate as the peroxide addition.

As discussed in copending U.S. application Ser. No. 08/379,202 filed Jan. 27, 1995, the contents of which are incorporated herein by reference, the biocatalytic reaction of a 2,6-disubstituted phenol yields both the biphenol product and the corresponding quinone in a first stage with the subsequent reduction of the quinone to the desired diol at a higher temperature in a second stage. The reducing agent is, preferably, the phenolic substrate from which the quinone is derived. The quinone byproduct may also be encountered in the present method. The quinone can be reduced by either the phenolic substrate or the radical transfer agent. The biocatalytic reaction of the 2,4-disubstituted phenol yields the desired tetrasubstituted phenol without the formation of the quinone.

The concentration of the aromatic compound used in the reaction is not particularly critical. Typically, it will be used in amounts up to about 3 molar but typically about 1 to 2 molar will be sufficient.

The present invention finds its most valuable application in reacting aromatic compounds which are 2,4- or 2,6-disubstituted. The substituents defined by $R^1$ and $R^2$ in formula (I) may be further defined as an alkyl group of about 1 to 8 carbon atoms such as methyl, ethyl, butyl, tert-butyl, hexyl, etc.; an aryl group of about 6 to 10 carbon atoms such as phenyl, naphthyl, phenyl containing alkyl substituents; an alkenyl group containing about 2 to 8 carbon atoms and having one or more sites of unsaturation; alkynyl group containing about 2 to 8 carbon atoms and having 2 or more sites of unsaturation; an alicyclic group of about 5 to 10 carbon atoms such as cyclopentane, cyclohexane, cyclooctane, methyl cyclopentane, etc.; an alkoxy group of about 1 to 8 carbon atoms such as methoxy, ethoxy, butoxy, etc,; an aryloxy group of about 6 to 10 carbon atoms such as phenoxy, methylphenoxy, ethylphenoxy, butylphenoxy, etc.; a formyl group; a dialkylamino group in which the alkyl group has about 1 to 8 carbon atoms, or a diarylamino group in which the aryl group has about 6 to 10 carbon atoms such as phenyl, methylphenyl, ethylphenyl, etc.

The radical transfer agent useful in the present invention is any compound which is a substrate for the enzyme, i.e., any compound which reacts with the active site of the enzyme to form a radical which in turn abstracts a hydrogen atom from the substituted or more substituted aromatic substrate to initiate formation of the dimers. Preferably, the radical transfer agent is a phenolic compound in which the hydroxy hydrogen atom is abstracted by the peroxidase and which generates a radical which is effective in abstracting a hydrogen atom from the aromatic compound. Most preferably, the radical transfer agent is phenol but other phenols, thiophenols, or anilines can be used. Examples of radical transfer agents include mono-alkyl phenols, e.g., para-t-butylphenol, o-cresol, m-cresol, p- cresol, p-butylphenol, etc.; p-phenylphenol; bisphenol-A; halogenated phenols such as p-chlorophenol, etc. are also useful. It is proposed that the radical transfer agents are not incorporated into the dimer because the radical generated by the radical transfer agent abstracts a hydrogen from the substituted aromatic substrate which results in a phenoxy radical which is more stable than the radical generated by the radical transfer agent. The radical transfer agent is regenerated whereas the more stable radical from the aromatic substrate can dimerize.

The amount of radical transfer agent employed will depend on the nature and concentration of the substituted aromatic compound and generally will be about 1 to 20%, typically about 2 to 4% based upon the amount of the aromatic compound of formula (I).

A variety of peroxidases are useful in the present invention. The preferred peroxidase is soybean peroxidase; however, other peroxidases such as horseradish peroxidase and peroxidases from other legumes such as peroxidases from peas, guar, beans, garbanzo beans and runner beans may also be used. It is also believed that peroxidases from rice and certain malvaceous plants, such as cotton may be useful and that microbial peroxidases may also be useful as well as synthetic enzymes and enzymes produced by recombinant DNA methods.

The amount of enzyme used will depend on a number of factors such as the particular substituted aromatic used, the reaction temperatures, pH, etc. Generally, the amount of enzyme useful in the present invention can range from about 10 to 400 purpurogallin units per gram of the aromatic compound. It is generally desirable to prepare an enzyme solution at an approximate concentration such that it can be added in an approximately equal volume to the solution of the phenol monomer, but this is not necessary and, in many cases, may vary greatly.

The peroxide used in the present invention is typically hydrogen peroxide, but other peroxides may be used. Examples of other potentially useful peroxides include methyl peroxide, ethyl peroxide, etc. The peroxide is reacted in a total amount of about 0.1 to 2.5 moles per mole substituted aromatic substrate and, more typically, about 0.1 to 1.0 mole per mole of the aromatic compound. Depending upon the nature of the aromatic compound, it may be reacted neat or as a solution. Because high concentration of peroxide may inhibit the reaction, the hydrogen peroxide is preferably dissolved in water in a concentration of about 1 mM to 10 mM and then added to the reaction medium at a constant rate or at a rate which decreases from an initial rate as the amount of monomer decreases as described next. The initial rate of addition (moles/min.) of the peroxide solution is set at about twice the average reaction rate. Typically, the peroxide is initially added at a pump rate of about 7 millimoles per mole of substituted aromatic substrate/min. and, thereafter, the rate of addition is adjusted downwardly for the decrease in the rate of reaction which accompanies the reaction of the substituted aromatic substrate of the substitute aromatic substrate and the lower aromatic substrate concentration. The rate of downward adjustment is controlled such that the peroxide concentration in the reaction does not exceed about 12 millimolar and, preferably, about 3 to 5 millimolar.

The reaction is conducted in an aqueous medium such as water or a mixture of water and an organic solvent which may be water-miscible or water-immiscible. Where the medium is a mixture of water and organic solvent, the organic solvent is typically present in an amount up to about 60% and preferably up to about 30%. Representative examples of useful organic solvents include hexane, trichloromethane, methyl ethyl ketone, ethyl acetate, butanol, ethanol, methanol, dioxane, acetonitrile, tetrahydrofuran (THF), dimethyl formamide methyl formate, acetone, n-propanol, isopropanol, t-butyl alcohol, etc. and mixtures thereof.

Since substituted aromatic monomers are generally not soluble in water, an elevated temperature of about 35° C. to 60° C. and more typically 45° C. to 60° C. is used to disperse the aromatic substrate in the reaction medium followed by thorough mixing. Also, it may be desirable to add a surfactant to the substrate reaction medium in order to improve the dispersion of the aromatic substrate and thereby improve the reaction.

The tetrasubstituted aromatic dimer prepared in accordance with the present invention are useful in a variety of applications such as in making epoxy resins, flame retardants, antioxidants, polyesters, polycarbonates, and in other applications in which aromatic dimers are used.

The invention is illustrated in more detail by the following non-limiting examples:

EXAMPLE 1

85 Grams (410 mmoles) 2,4-di-tert-butylphenol, 0.5 grams (5 mmoles) phenol, 40 ml (15,000 ppu) soybean peroxidase solution (375 ppu/ml) and 90 ml deionized water were added to a water jacketed three-neck round bottom flash, equipped with a mechanical stirrer, and heated to 55° C. Sodium hydroxide was also added over the course of the reaction to maintain the pH between 7.5 and 8.5. The reaction mixture was neutralized using hydrochloric acid and then filtered to remove unreacted monomer and biproducts. After drying, 81 grams of 2,4-di-tert-butyl-phenol dimer was obtained with a yield of 95%.

EXAMPLE 2

122 Grams of 2,6-dimethylphenol and 6 grams of phenol were added to 200 ml of soybean peroxidase solution (17,080 ppu units) while stirring at 48° C. To the reaction mixture, 36 ml of 35% hydrogen peroxide was added over six hours. Upon completion of the addition of the hydrogen peroxide, the reaction mix was heated at 100 C for 1.5 hours. The product was collected by filtration and washed twice with 200 ml of toluene for 30 minutes at 30° C. to remove unreacted monomer and any polyphenylene oxide. After drying, 88 grams of tetramethyl biphenol, 24 grams of monomer and 8 grams of polyphenylene oxide were collected.

EXAMPLE 3

122 Grams of 2,6-dimethylphenol and 6 grams of phenol dissolved in 60 ml of methanol were added to 140 ml of soybean peroxidase solution (9,150 ppu units) while stirring at 51° C. To the reaction mixture, 32 ml of 35% hydrogen peroxide was added over three hours. Upon completion of the addition of the hydrogen peroxide, the methanol was removed by distillation and washed twice with 200 ml of toluene at 30° C. for 30 minutes. After drying, 67 grams of tetramethyl biphenol, 35 grams of monomer and 19 grams of polyphenylene oxide were collected.

Having described the invention in detail and by reference to preferred embodiments thereof, it will be apparent that modifications and variations are possible without departing from the scope of the invention defined in the appended claims.

What is claimed is:

1. A process for the dimerization of an aromatic compound having the formula (I)

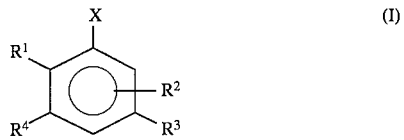

(I)

wherein X represents —OH, —SH or —NHR where R is H, an alkyl group or an aryl group; $R^1$ and $R^2$ represent an alkyl group, an aryl group, an alkenyl group, an alkynyl group, an alicyclic group, a halogen atom, an alkoxy group, an aryloxy group, a hydroxy group, a formyl group, or an amino group; $R^3$ and $R^4$ can have the same definition as $R^1$ and $R^2$ and may additionally represent a hydrogen atom; which comprises reacting said substituted aromatic compound in the presence of a peroxidase enzyme, a peroxide and a radical transfer agent in an aqueous medium.

2. The process of claim 1 wherein said aromatic compound is a 2,4- or 2,6- disubstituted aromatic compound.

3. The process of claim 2 wherein said 2,4- or 2,6- disubstituted aromatic compound is a 2,4- or 2,6-dialkylphenol or a 2,4- or 2,6-diarylphenol.

4. The process of claim 1 wherein said peroxidase enzyme is soybean peroxidase.

5. The process of claim 1 wherein said peroxide is hydrogen peroxide.

6. The process of claim 1 wherein said radical transfer agent is selected from the group consisting of phenol, p-phenylphenol, bisphenol-A, p-chlorophenol, para-t-butylphenol, and cresol.

7. The process of claim 6 wherein said radical transfer agent is phenol.

8. The process of claim 1 wherein said aqueous medium is water or a mixture of water and an organic solvent, said organic solvent being water miscible or water immiscible.

9. The process of claim 1 wherein said radical transfer agent is present in an amount of about 1 to 20% by weight of said substituted aromatic compound.

10. The process of claim 1 wherein said peroxidase is present in an amount of about 10 to 400 purpurogallin units per gram of said aromatic compound.

11. The process of claim 1 wherein said peroxide is added at a rate which decreases from an initial rate as the amount of substituted phenolic compound in said medium decreases such that the concentration of peroxide in said medium does not exceed about 12 millimolar.

12. The process of claim 1 wherein said reaction is carried out at a temperature of about 0° to 60° C.

13. A process for the oxidative coupling of 2,4- or 2,6-di-tert-butyl phenol which comprises reacting said 2,4- or 2,6-di-tert-butyl phenol in the presence of about 1 to 20% by weight of a radical transfer agent based on said 2,4- or 2,6-di-tert-butyl phenol, about 10 to 400 purpurogallin units soybean peroxidase per gram of said 2,4- or 2,6-di-tert-butyl phenol, and hydrogen peroxide, at about 0° to 60° C. to provide a dimer of said 2,4- or 2,6-di-tert-butyl phenol.

14. The process of claim 12 wherein said radical transfer agent is phenol.

* * * * *